US00PP12002P2

(12) United States Plant Patent
Masuda

(10) Patent No.: US PP12,002 P2
(45) Date of Patent: Jul. 17, 2001

(54) PHLOX PLANT NAMED 'NIHON KAKI VARIEGATED'

(75) Inventor: Tamotsu Masuda, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/460,002

(22) Filed: Dec. 13, 1999

(51) Int. Cl.[7] ..... A01H 5/00

(52) U.S. Cl. ..... Plt./320

(58) Field of Search ..... Plt./320

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Phlox plant named 'Nihon Kaki Variegated', characterized by its upright plant habit; unique green and ivory variegated foliage; attractive pink flowers with darker pink centers; and good garden performance.

1 Drawing Sheet

BACKGROUND OF THE INVENTION

The present invention relates to a new and distinct cultivar of Phlox plant, botanically known as *Phlox paniculata*, and hereinafter referred to by the cultivar name Nihon Kaki Variegated.

The new Phlox is a naturally-occuring whole plant mutation of an unidentified selection of *Phlox paniculata* (not patented) with solid green leaves. The new Phlox was discovered and selected by the Inventor in 1991, within a population of plants of the unidentified *Phlox paniculata* selection grown in a cultivated area in Kawaguchi City, Japan. The new Phlox was selected on the basis of its unique variegated foliage.

Asexual reproduction of the new cultivar by terminal cuttings taken at Kawaguchi City, Japan, and Irvine, Calif., has shown that the unique features of this new Phlox are stable and reproduced true to type in successive generations.

SUMMARY OF THE INVENTION

Plants of the cultivar Nihon Kaki Variegated have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Nihon Kaki Variegated'. These characteristics in combination distinguish 'Nihon Kaki Variegated' as a new and distinct cultivar:

1. Upright plant habit.
2. Unique green and ivory variegated foliage.
3. Attractive pink flowers with darker pink centers.
4. Good garden performance.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors.

The photograph at the top of the sheet comprises a close-up view of typical flowering stems of the new Phlox.

The photograph at the bottom of the sheet comprises a close-up view of typical flowers and leaves of the new Phlox. The age and the environmental conditions of the plants depicted in the photographs are the same as those disclosed in the detailed botanical description.

DETAILED BOTANICAL DESCRIPTION

In the following description, color references are made to The Royal Horticultural Society Colour Chart except where general terms of ordinary dictionary significance are used.

Plants used for the description were about 5 months old and were grown under outdoor production conditions during the spring and early summer in Irvine, Calif.

Botanical classification: *Phlox paniculata* cultivar Nihon Kaki Variegated.

Parentage: Naturally-occurring whole plant mutation of an unidentified selection of *Phlox paniculata* (not patented).

Propagation:

*Type.*—By stem cuttings.

*Time to initiate roots.*—About 14 days at 22° C.

*Time to develop roots* (*time to produce a rooted liner*).—About 28 days at 22° C.

*Root appearance.*—Fibrous, fine.

Plant description:

*Crop time.*—From cuttings, about 16 to 20 weeks are required to produce a flowering plant in a one-gallon container.

*Form.*—Strong, upright and tall perennial herb.

*Plant height.*—About 36 cm.

*Plant width.*—About 26 cm.

*Vigor.*—Moderate.

*Lateral branches.*—Quantity: Pinching enhances lateral branch development; laterals may form at every node. Diameter: About 2 mm. Internode length: About 4.4 cm. Texture: Glabrous. Color: 146A.

*Foliage description.*—Leaves simple, generally symmetrical, opposite and long persisting. Tolerant to stresses. Length: About 8.7 cm. Width: About 2.2 cm. Shape: Linear. Apex: Acute. Base: Attenuate, sessile. Margin: Entire. Texture: Leathery, smooth; midvein prominent on lower surface. Color: Actual variegation patterns vary. Young leaves typically are more variegated than mature leaves. Reddish purple anthocyanin development may occur near margins. Young foliage, upper surface: Margin, 158C; center, close to 147B; random spots, 147C. Young foliage, lower surface: Margin, 158D; center, close to 147B. Mature foliage, upper surface: Margin, close to 158C; center, 147A to 147B; random spots, 147C. Mature foliage, lower surface: Margin, close to 158C to 158D; center, 147A to 147B.

Flower description:

*Flower type and habit*—Single round flowers arranged in terminal panicles; flowers face outward or upright. Panicles globular or pyramidal in shape. Freely flowering. Corolla, salverform, 5-lobed; calyx five-cleft. Individual flowers last about three days on the plant. Not persistent.

*Natural flowering season.*—Continuously flowering from mid-summer through fall.

*Quantity.*—Very freely flowering with numerous flowers per panicle.

*Fragrance.*—Sweet, nectar-like.

*Flower buds.*—Length: About 1.5 cm. Diameter: About 3 mm. Shape: Tubular. Rate of opening: About one day. Color: Initially greenish white to white, then pink, 62B to 62C.

*Flowers size.*—Diameter: About 2.4 cm. Depth: About 2.2 cm. Tube length: About 1.7 cm. Tube diameter: About 2 mm.

*Petals.*—Quantity: Five, fused. Length (beyond throat): About 1 cm. Width: About 1 cm. Shape: Spatulate to rhomboidal. Apex: Rounded acute. Margin: Entire. Texture: Smooth, satiny. Tube is pubescent. Color: When opening and fully opened, upper surface: 62A; base, 67A. When opening and fully opened, lower surface: 62C to 62D. Tube: 62C. Throat: 62D.

*Calyx.*—Calyx length: About 8 mm. Calyx diameter: About 2.5 mm. Shape: Campanulate; sepals, very narrow and fused at base. Sepal quantity: Five. Sepal apex: Sharply acute. Sepal margin: Entire. Sepal texture: Smooth. Sepal color, upper and lower surfaces: Whitish green (color not represented in R.H.S. Colour Chart).

*Pedicel.*—Strength: Flexible, but strong. Length: About 3 mm. Diameter: About 1 mm. Color: Close to 144A.

*Reproductive organs.*—Androecium: Stamen number: Five. Anther shape: Linear. Anther size: About 2 by 0.5 mm. Pollen: Moderate. Pollen color: 8C. Gynoecium: Pistil length: About 1.7 cm. Stigma color: Yellowish. Style color: Light green at base, dark pink towards apex. Ovary color: 144A.

*Seed development.*—Seed development has not been observed.

Disease resistance: Under commercial conditions, resistance to pathogens common to *Phlox paniculata* has been observed.

It is claimed:

1. A new and distinct cultivar of Phlox plant named 'Nihon Kaki Variegated', as illustrated and described.

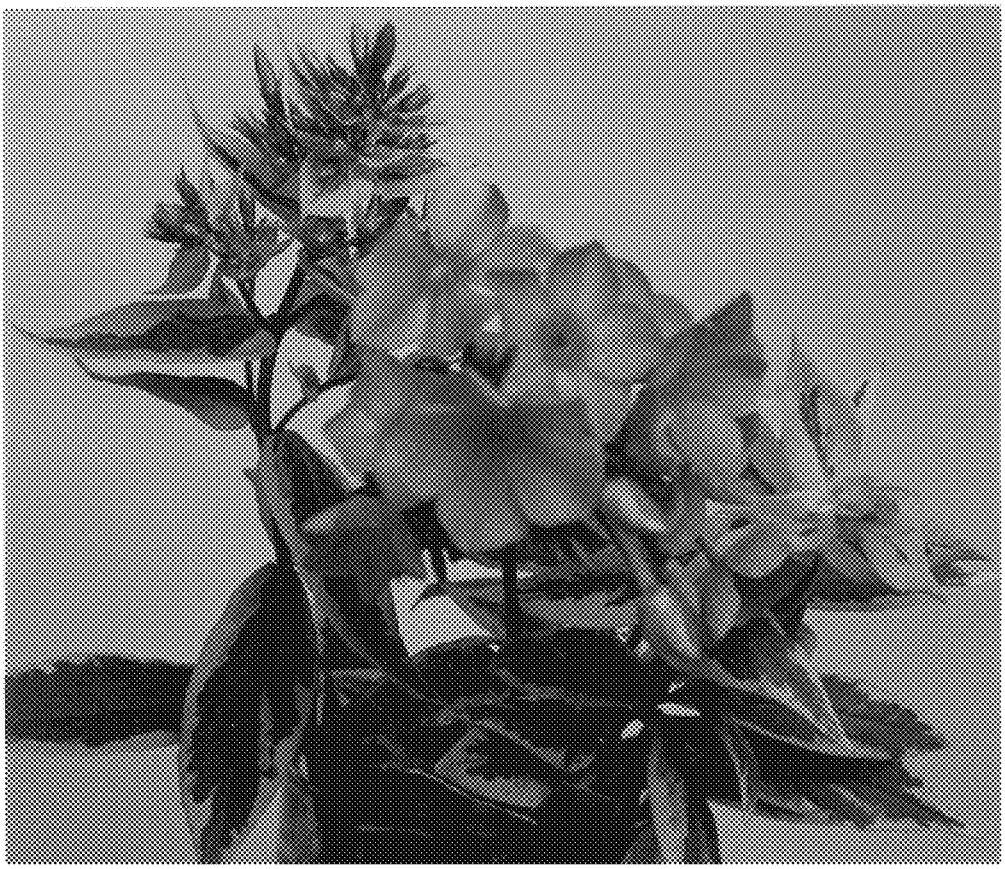
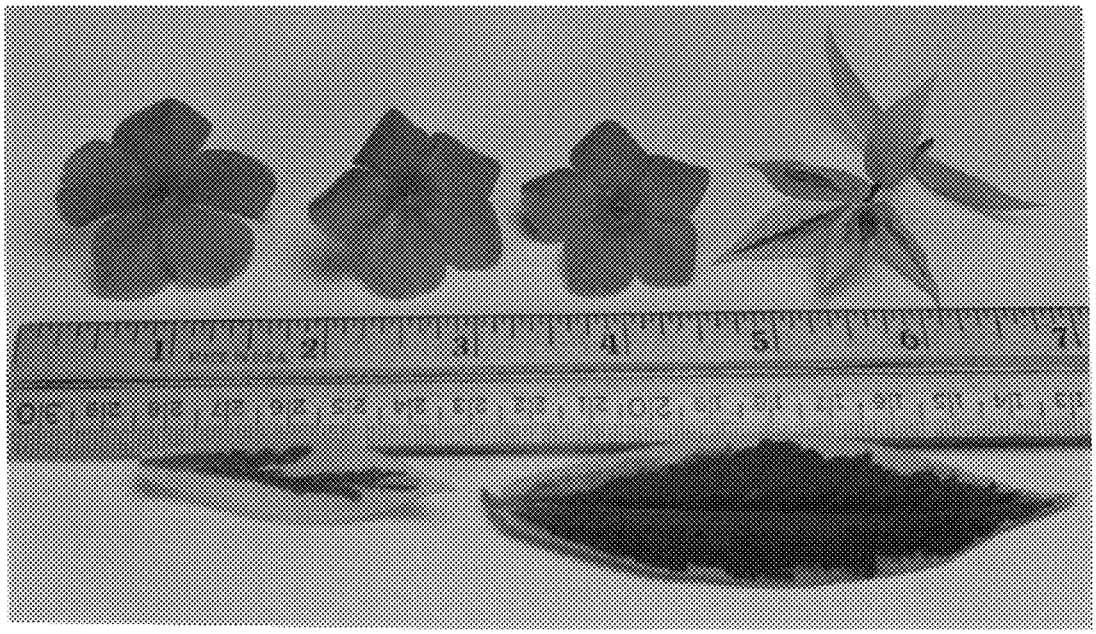

* * * * *